United States Patent
Schug et al.

(10) Patent No.: US 12,163,961 B2
(45) Date of Patent: Dec. 10, 2024

(54) BTEX METABOLITES DERIVATIZATION KIT AND COMPOSITION

(71) Applicant: Board of Regents, The University of Texas System, Austin, TX (US)

(72) Inventors: Kevin Albert Schug, Southlake, TX (US); Yehia Zakaria Mahmoud Youssef Baghdady, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 123 days.

(21) Appl. No.: 17/972,535

(22) Filed: Oct. 24, 2022

(65) Prior Publication Data
US 2023/0069226 A1 Mar. 2, 2023

Related U.S. Application Data

(62) Division of application No. 16/308,211, filed as application No. PCT/US2017/036820 on Jun. 9, 2017, now Pat. No. 11,506,669.

(60) Provisional application No. 62/348,133, filed on Jun. 9, 2016.

(51) Int. Cl.
G01N 33/58 (2006.01)
C07D 213/38 (2006.01)
C07D 213/643 (2006.01)
G01N 30/72 (2006.01)
G01N 30/02 (2006.01)

(52) U.S. Cl.
CPC .......... *G01N 33/58* (2013.01); *C07D 213/38* (2013.01); *C07D 213/643* (2013.01); *G01N 30/7266* (2013.01); *G01N 2030/027* (2013.01); *G01N 2560/00* (2013.01)

(58) Field of Classification Search
None
See application file for complete search history.

(56) References Cited

U.S. PATENT DOCUMENTS

| 4,990,458 A | 2/1991 | Rosenfeld et al. |
| 2004/0014196 A1 | 1/2004 | Coates et al. |
| 2012/0319042 A1 | 12/2012 | Hoag et al. |

OTHER PUBLICATIONS

Callaghan "Metabolomic investigations of anaerobic hydrocarbon-impacted environments", Current Opinion in Biotechnology, vol. 24, 2013, pp. 506-515.
Rothman et al, "Urinary excretion of phenol, catechol, hydroquinone, and muconic acid by workers occupationally exposed to benzene", Occup Environ Med., vol. 55, 1998, pp. 705-711.
(Continued)

*Primary Examiner* — Xiaoyun R Xu
(74) *Attorney, Agent, or Firm* — Winstead PC

(57) ABSTRACT

A kit or composition for in situ simultaneously derivatization of 14 phenol and carboxylic acid metabolites of benzene, toluene, ethyl benzene, and xylene (BTEX) in a urine sample is disclosed. The derivatization imparts a positive charge to phenol and carboxylic acid for subsequent LC-MS analysis. Limit of detection reached part-per-trillion levels for o-Cresol and part-per-billion levels for the remaining BTEX metabolites. BTEX metabolites can be detected in less than 35 mins according to one embodiment of the invention. Methods, kits and compositions disclosed herein can be used for in situ simultaneous derivatization of phenol and carboxylic acid in aqueous solution in general.

6 Claims, 8 Drawing Sheets

(56) References Cited

OTHER PUBLICATIONS

White et al.; "Forensic Analysis by Comprehensive Rapid Detection of Pathogens and Contamination Concentrated in Biofilms in Drinking Water Systems for Water Resource Protection and Management", Environmental Forensics, vol. 4, 2003, pp. 63-74.
International Search Report in related application No. PCT/US17/36820, dated Sep. 6, 2017.
Yang, Wen-Chu et al.; "Enhancement of the LC/MS Analysis of Fatty Acids through Derivatization and Stable Isotope Coding"; Analytical Chemistry; vol. 79 No. 14; Jul. 15, 2007; pp. 5150-5157.
Beinhauer, Jana et al.; "Bulk derivatization and cation exchange restricted access media-based trap-and-elute liquid chromatography-mass spectrometry method for determination of trace estrogens in serum"; Analytic Chimica Acta; vol. 858; 2015; pp. 74-81.
"Phenomenex Expands Selectivity of Kinetex® Core-Shell Line with New Biphenyl Columns"; American Laboratory; Mar. 3, 2014; 2 pages.

Biophenyl

PFP Propyl

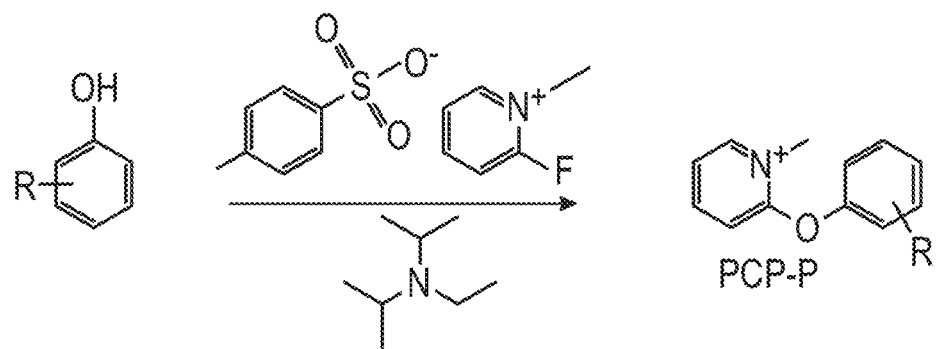
FIG. 3A
1st Step
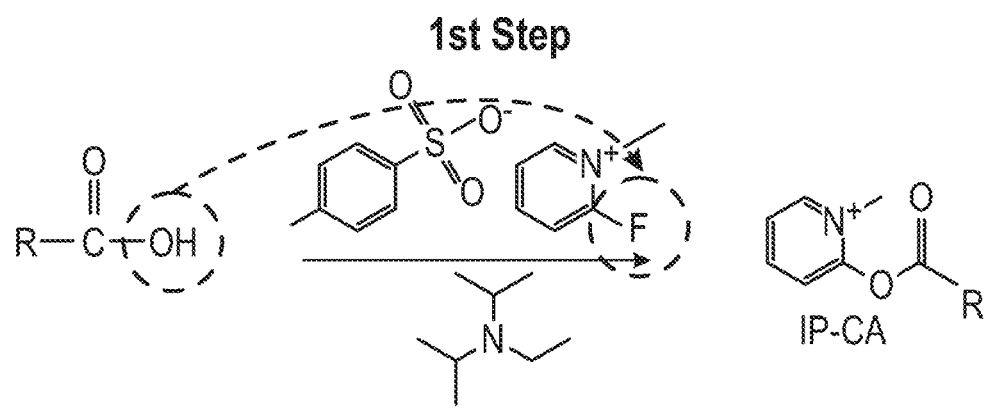
2nd Step
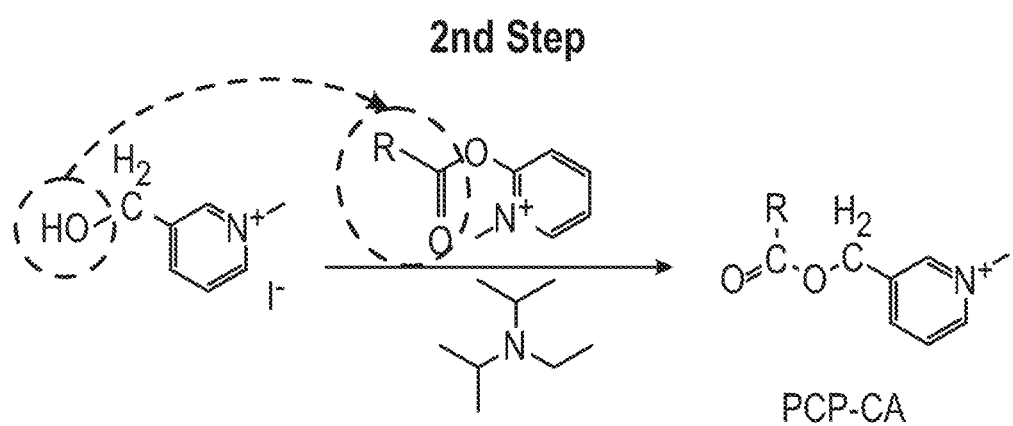
FIG. 3B

MRM Transitions for Derivatized Metabolites and their Deuterated Analogs

| Parent Compound | Metabolites | Quantifier MRM, m/z Transition (CE*, V) | Qualifier MRM transitions, m/z | Internal Standard MRM transition, m/z (CE*, V) |
|---|---|---|---|---|
| Benzene | MU<br>PMA<br>Phenol<br>Catechol | 177.0>107.1 (-19)<br>344.8>235.1 (-22)<br>186.0>110.05 (-24)<br>202.0>110.1 (-27) | 177.0>92.1, 177.0>122.1<br>344.8>107.1, 344.8>124.1<br>186.0>77.1, 186.0>51.1<br>202.0>93.1, 202.0>78.1 | 179.1>107.0 (-20)<br>350.2>235.1 (-22)<br>189.0>111.1 (-26)<br>207.0>111.1 (-27) |
| Toluene | BA<br>HA<br>BMA<br>o-Cresol<br>p-Cresol | 228.0>107.0 (-28)<br>285.1>124.1 (-23)<br>359.2>235.1 (-22)<br>200.0>110.1 (-24)<br>200.0>110.1 (-25) | 228.0>105.1, 228.0>92.1<br>285.1>107.1, 285.1>92.1<br>359.2>107.1, 359.2>124.1<br>200.0>91.1, 200.0>65.1<br>200.0>91.1, 200.0>65.1 | 233.0>107.1 (-29)<br>290.2>124.1 (-25)<br>364.2>107.1 (-45)<br>207.0>98.2 (-28)<br>207.0>111.1 (-28) |
| Ethylbenzene, Styrene | MA<br>PGA | 258.1>124.1 (-25)<br>256.0>107.1 (-22) | 258.1>107.1, 258.1>92.1<br>256.0>92.1, 256.0>106.1 | 263.2>124.1 (-25)<br>261.1>107.1 (-25) |
| Xylenes | 2MHA<br>3MHA + 4MHA | 299.0>107.1 (-32)<br>299.0>124.1 (-25) | 299.0>124.2, 299.0>92.1<br>299.0>107.1, 299.0>92.1 | 306.2>107.1 (-32)<br>306.2>107.0 (-33) |

FIG. 4

*CE: Collision Energy

Predictive Coded Polynomial Models

| Response | Intercept | A* | B** | C*** | AB | AC | BC | A^2 | B^2 | C^2 | A^2B | A^2C |
|---|---|---|---|---|---|---|---|---|---|---|---|---|
| Square Root (Catechol) | 1163.84 | -326.27 | 119.01 | 356.57 | -6.35 | 95.35 | -48.93 | 51.81 | 1.35 | -147.00 | | |
| Phenylmercapturic Acid | 2665.15 | 83.43 | 1711.09 | -1004.59 | 368.29 | 76.88 | -767.13 | -355.87 | 159.51 | 272.83 | | |
| Log10 (Muconic Acid) | 4.5 | 0.27 | 0.17 | -0.26 | 0.10 | -0.12 | | 0.11 | -0.14 | 0.16 | | |
| 3-&4-MethylHippuric Acids | 6195.70 | 135.74 | 2645.55 | -3016.33 | 1454.19 | -109.23 | -1151.44 | -705.72 | | 1482.30 | 1348.35 | 1482.97 |

*A: FMP Concentration (mg mL$^{-1}$)
**B: CMP Concentration (mg mL$^{-1}$)
***C: TEA Volume (μL)

FIG. 6

BTEX METABOLITES DERIVATIZATION KIT AND COMPOSITION

CROSS-REFERENCE TO RELATED APPLICATIONS

This patent application is a divisional of U.S. patent application Ser. No. 16/308,211 filed on Dec. 7, 2018. U.S. patent application Ser. No. 16/308,211 is a national stage entry of PCT/US17/36820, which was filed on Jun. 9, 2017 and claims priority from U.S. Provisional Patent Application 62/348,133, filed Jun. 9, 2016. The entire disclosures of the aforementioned applications are incorporated herein by reference.

FIELD OF THE INVENTION

The present disclosure is directed to an in situ BTEX (acronym of benzene, toluene, ethylbenzene, and xylenes) metabolite derivatization kit. The present disclosure is also directed to a composition for one-pot-charge-reversal simultaneous derivatization of phenol and carboxylic acid and method of making and using the composition. The present disclosure further directs to detection of BTEX metabolites in biological samples using the kit and compositions disclosed herein.

BACKGROUND

BTEX metabolites are usually present at very low levels in biological samples such as urine, serum, and plasma. Moreover, these biological samples comprise interferants such as proteins, lipids, and salts. To make the situation more challenging, BTEX metabolites in biological samples comprises phenol and carboxylic acid, which are difficult to detect at low levels under normal electrospray ionization-mass spectrometry (ESI-MS) conditions.

What is needed is an effective method of detecting BTEX metabolites in biological and environmental samples.

SUMMARY

In one aspect, disclosed herein is a composition for derivatizing phenol and carboxylic acid simultaneously in an aqueous sample. The composition comprises, a first pyridinium salt capable of forming a positively charged pyridinium derivative of the phenol (PCP-P) as well as an intermediate pyridinium derivative of the carboxylic acid (IP-CA), a second pyridinium salt capable of reacting with the IP-CA to form a positively charged pyridinium derivative of the carboxylic acid (PCP-CA), and an organic base. The first pyridinium salt has a structure of Formula I, where Y=I⁻, BF₄⁻ or

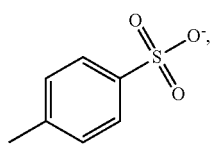

R=—CH₃ or —C₂H₅, and X=F⁻, Cl⁻ or Br⁻

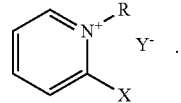

Formula I

The second pyridinium salt has a structure of Formula II, where $R_1$=—CH₃ or —C₂H₅; $R_2$=—CH₂— or —C₂H₄⁻; and Y⁻=I⁻ or BF₄⁻.

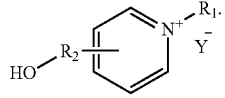

Formula II

The amount of the first pyridinium salt in the composition is at least 200 times higher than the phenol amount in the sample, the amount of the second pyridinium salt is at least 16 times higher than the carboxylic acid amount, and the amount of the organic base is at least about 0.01 times of the combined amount of the first and the second pyridinium salt.

The organic base is selected from a group consisting of triethyl amine, N,N-Diisopropylethylamine, tributylamine, trimethylamine. In one embodiment in the composition, the first pyridinium salt is 2-Fluoro-1-methylpyridinium p-toluenesulfonate (2-FMP), the second pyridinium salt is 3-carbinol-1-methylpyridinium iodide (3-CMP), and the organic base is triethyl amine (TEA). In one embodiment, the composition is capable of derivatizing about 3.5 nanogram/mL to about 7.8 μg/mL of phenol and carboxylic acid and the first pyridinium salt is 21-35 mg/mL of 2-fluoro-1-methylpyridinium p-toluenesulfonate (2-FMP), the second pyridinium salt is 24-40 mg/mL of 3-carbinol-1-methylpyridinium iodide (3-CMP), and the organic base is 4.5-7.5 μL of triethyl amine. In one embodiment, the composition comprises about 28 mg/mL of 2-fluoro-1-methylpyridinium p-toluenesulfonate (2-FMP) in acetonitrile, about 32 mg/mL of 3-carbinol-1-methylpyridinium iodide (3-CMP) in acetonitrile, and about 6 μL of triethyl amine (TEA).

The composition disclosed herein can be adopted in a kit format. In one embodiment, disclosed herein is a kit or composition capable of derivatizing in situ simultaneously about 3.5 nanogram/mL to about 7.8 μg/mL of 14 of phenol and carboxylic acid metabolites of benzene, toluene, ethylbenzene, and xylenes (BTEX). The kit or composition comprises about 28 mg/mL of 2-fluoro-1-methylpyridinium p-toluenesulfonate (2-FMP) in acetonitrile to form a positively charged pyridinium derivative of the phenol (PCP-P) as well as an intermediate pyridinium derivative of the carboxylic acid (IP-CA), about 32 mg/mL of 3-carbinol-1-methylpyridinium iodide (3-CMP) in acetonitrile to form a positively charged pyridinium derivative of the carboxylic acid (PCP-CA) from the IP-CA, and about 6 μL of triethyl amine (TEA).

A kit or composition capable of derivatizing in situ simultaneously phenol and carboxylic acid in a sample is disclosed. The kit or composition comprises a first pyridinium salt capable of forming a positively charged pyridinium derivative of the phenol (PCP-P) as well as an intermediate pyridinium derivative of the carboxylic acid (IP-CA), a second pyridinium salt capable of reacting with the IP-CA to form a positively charged pyridinium derivative of the carboxylic acid (PCP-CA), and an organic base. The first pyridinium salt has a structure of Formula I, Y=I−, $BF_4^-$

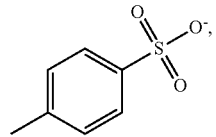

R=—$CH_3$ or —$C_2H_5$, and X=F−, Cl− or Br−

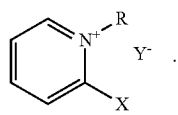

Formula I

The second pyridinium salt has a structure of Formula II, where $R_1$=—$CH_3$ or —$C_2H_5$; $R_2$=—$CH_2$— or —$C_2H_4$—; and Y−=I− or $BF_4^-$; and Y−=I− $BF_4^-$.

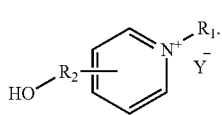

Formula II

In the kit or composition, the amount of the first pyridinium salt is at least 200 times higher than the phenol amount in the sample, the amount of the second pyridinium salt is at least 16 times higher than the carboxylic acid amount, and the amount of the organic base is at least about 0.01 times of the combined amount of the first and the second pyridinium salt. In one embodiment, the kit or composition is capable of derivatizing about 3.5 nanogram/mL to about 7.8 μg/mL of phenol and carboxylic acid and the first pyridinium salt is 21-35 mg/mL of 2-Fluoro-1-methylpyridinium p-toluenesulfonate (2-FMP), the second pyridinium salt is 24-40 mg/mL of 3-carbinol-1-methylpyridinium iodide (3-CMP), and the organic base is 4.5-7.5 μL of triethylamine. The organic base selected from a group consisting of triethylamine, N,N-Diisopropylethylamine, tributylamine, trimethylamine.

In a second aspect, disclosed herein is a method of detecting phenol and carboxylic acid in an aqueous sample using the kit or composition disclosed herein. In one embodiment, the sample comprises BTEX metabolites that comprises phenol and carboxylic acid. The method comprises adding the composition or composition from the kit to the sample to derivatize the phenol and carboxylic acid in the sample in situ to form corresponding PCP-P and PCP-CA in a reaction mixture and subjecting the reaction mixture to LC-ESI-MS/MS to separate and analyze the PCP-P and PCP-CA to determine the quantity and molecular weight of the corresponding phenol and carboxylic acid. In one embodiment, the separation of the PCP-P and PCP-CA is performed on a functionalized reverse phase column. The sample is a urine, serum, plasma, or blood sample. In one embodiment, the sample is a urine sample and the column is a biphenyl functionalized reverse phase column. In one embodiment, the method further comprises pre-treating the PCP-P and PCP-CA reaction mixture on a restricted access media trap column for LC-ESI-MS/MS separation and analysis.

The feature or features of one embodiment may be applied to other embodiments, even though not described or illustrated, unless expressly prohibited by this disclosure or the nature of the embodiments.

Details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears.

FIG. 3A illustrates derivatization of phenol according to one embodiment of the invention.

FIG. 3B illustrates derivatization of carboxylic acid according to one embodiment of the invention.

FIG. 4 shows MRM transitions for derivatized metabolites and their deuterated analogs according to one embodiment of the invention.

FIG. 6 shows predictive coded polynomial models used according to one embodiment of the invention.

DETAILED DESCRIPTION

Figure 1:
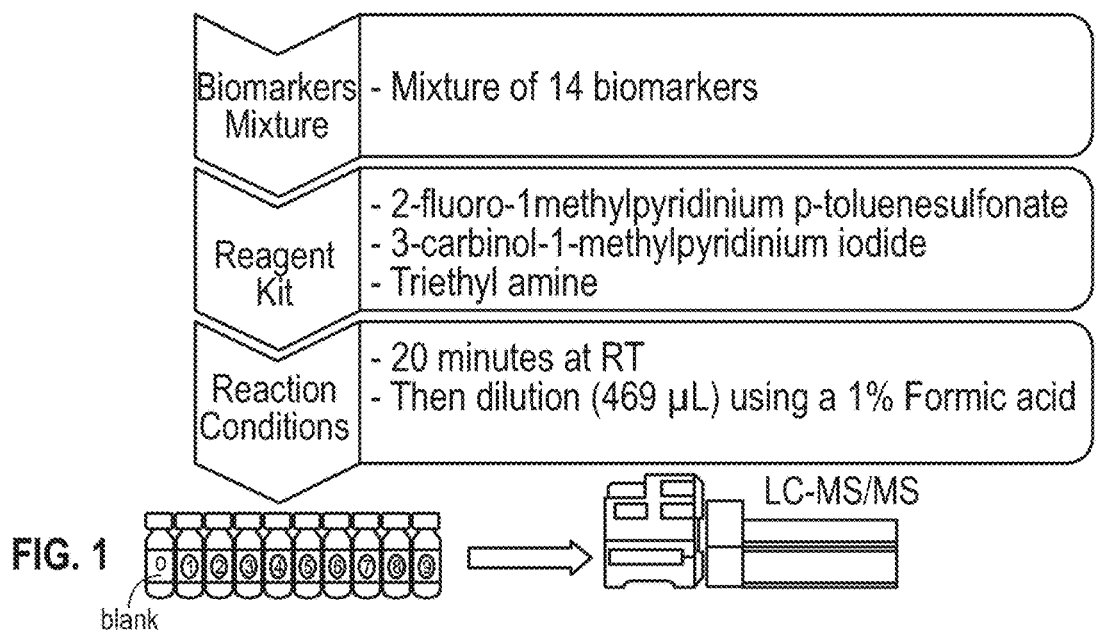
FIG. 1 is a schematic diagram of workflow sequence for the one-pot in situ derivatization kit disclosed herein according to one embodiment of the invention.

A charge-reversal-one-pot derivatization kit or composition was developed and applied to simultaneously derivatize BTEX metabolites in human urine over a wide concentration range. The derivatized BTEX metabolites can be directly subjected to LC-MS analysis in situ to qualitatively and quantitively determine the presence of BTEX metabolites in human urine. A series of fourteen carboxylic acid and phenol-bearing urinary metabolites of BTEX are derivatized with the kit or composition disclosed herein to enhance their chromatographic analysis and sensitivity for detection by liquid chromatography—electrospray ionization—tandem mass spectrometry (LC-ESI-MS/MS). Using the reagent kit or composition, the less responsive functional units on the molecules are converted to permanently positively-charged functional units. The kit or composition comprises three key components, including a basic catalyst, a first pyridinium salt capable of derivatizing phenol and a second pyridinium salt capable of derivatizing carboxylic acid. Urine sample diluted with acetonitrile was applied to the kit or composition to achieve derivatization under room temperature and short reaction time of less than 30 minutes. The derivatized BTEX metabolites are then directly analyzed using isotope dilution LC-ESI-MS/MS. The method was sensitive with limit of detection (LOD) ranged from 1.4 pg to 3.1 ng on column, accurate with mean accuracy from 85 to 114%, and precise with mean coefficient of variation from 1 to 14%. The entire method of derivatization followed by subsequent analysis takes less than 35 minutes at room temperature and multiple samples can be processed in parallel. The method disclosed herein is suitable for fully automated process and can be applied to routine high throughput analysis of very small volumes of urine samples. The methods disclosed herein can be used for example for metabolite profiling in a diagnostic measure for both short and long-team co-exposure by individuals to benzene, toluene, ethylbenzene and xylenes (BTEX).

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In some embodiments, the subject is a mammal such as a primate, for example, a human.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The present disclosure may be understood more readily by reference to the following detailed description of embodiments and to the Figures and their previous and following description.

Benzene, toluene, ethylbenzene, and xylenes (BTEX) are monoaromatic hydrocarbons which are ubiquitous in the surrounding environment. They are extensively used as solvents, as raw materials for the synthesis of pharmaceuticals and many other organic compounds, and as vital components of many industrial products including gasoline, paints, pesticides, plastics, and glues. Humans can be easily exposed to BTEX compounds through inhalation, skin absorption, and/or ingestion of contaminated food and water. Due to their high volatility, their vapors can easily contaminate air, water, and soil. BTEX exposure is not limited only to outdoor environments. Many studies have shown that indoor environments, e.g. furniture polishes, paintings, and household products, can provide higher exposure levels.

According to the International Agency for Research on Cancer (IARC), benzene is a group 1 carcinogen to humans, where increased incidence of leukemia has been reported, and ethylbenzene is a possible human carcinogen. Toluene and xylenes are not carcinogenic based on the current evidence but they are known to have neurotoxic effects. Because of toxic and carcinogenic effects of BTEX, the American Conference of Governmental Industrial Hygienists (ACGIH) has recommended their urinary metabolites to be used for the biological monitoring of occupational human exposure to BTEX. These urinary metabolites are useful biomarkers of internal dose for occupational and environmental exposure as they reflect absorption by all routes including for example inhalation, dermal, and ingestion and they have the advantages of long half-life, high specificity, low volatility, and non-invasive sampling of urine. Studies have shown that the relative proportions of urinary metabolites are affected by co-exposure as well as by the concentration, rate, and route of exposure. For instance, co-exposure to toluene and xylenes has been reported to reduce S-phenylmercapturic acid (PMA) in urine.

A list of BTEX compounds with their corresponding metabolites according to one embodiment of the invention are shown in Table 1 below. These metabolites were reported in literature due to their strong correlation with exposure levels across a wide range of BTEX concentrations and include: t,t-muconic acid (MU), S-phenylmercapturic acid (PMA), phenol, and catechol for benzene; hippuric acid (HA), S-benzylmercapturic acid (BMA), o-cresol, and p-cresol for toluene; mandelic acid (MA) and phenylglyoxylic acid (PGA) for ethylbenzene and methylhippuric acids (MHA) for xylenes. Benzoic acid (BA) is not reported as a direct biomarker of exposure to BTEX but its intake as benzoate, which is a common food preservative, can affect urinary background levels of HA (glycine conjugate of benzoic acid) in the human population. Lord et al. summarized different interpretation scenarios for different BA/HA ratios, other than those caused by exposure to BTEX. Hence, we added BA to our list of biomarkers to provide a method that can be adopted to obtain a complete diagnostic picture in toxicological studies. However, hippuric acid is not the only one of these metabolites which suffers from background levels in urine of non-exposed individuals. MU can be formed from dietary sorbic acid preservative. Benzyl mercapturic acid can be derived from benzyl alcohol which is present in many cosmetic products. Hippuric acid can be found in peaches, fruit juices, sodas, ketchup, and due to dietary intake of benzoate preservatives.

Simultaneous determination of multiple metabolites for each parent compound and not relying solely on a specific biomarker is desired. Moreover, adopting a multiple biomarkers approach will help to achieve more accuracy and specificity for evidence based decisions, provides a pattern match for single or co-exposures, shows co-exposure interaction effects on delay, suppression, or enhancement of formation and capture the variability through the studied population.

pounds. Some of BTEX urinary metabolites were not incorporated in each of the reported simultaneous determination methods and most of the reported methods focused only on either the carboxylic or phenolic metabolites to target as biomarkers. In case of GC, a derivatization procedure is usually employed for these polar metabolites, as shown for example in Analytical Chemistry Vol. 49, No. 6, May 1977, pg 832-834 by Bruce Davis. These traditional sample preparation methods are usually labor-intensive and can lead to sample loss, increased total analysis time, low recovery, and exposure to contaminants.

TABLE 1

| Benzene | Toluene | Ethylbenzene | Xylenes |
|---|---|---|---|
| trans-,trans-Muconic acid | Benzoic acid | Benzoic acid | 2-Methylhippuric acid |
| S-phenylmercapturic acid | Hippuric acid | Hippuric acid | 3-Methylhippuric acid |
| Phenol | S-benzylmercapturic acid | Mandelic acid | 4-Methylhippuric acid |
| Catechol | o-Cresol | Phenylglyoxylic acid | |
| p-Cresol | | | |

Several analytical methods have been published for the determination of urinary metabolites of one or more of the BTEX compounds such as paper and thin-layer chromatography, gas chromatography-flame ionization detection (GC-FJD), GC-MS, HPLC-UV, and HPLC-MS. However, few studies reported the simultaneous determination of 14 urinary metabolites derived from all BTEX compounds. Simultaneous determination of several metabolites would be particularly useful in cases of co-exposures. Approaches which have adopted simultaneous determination include capillary electrophoresis, HPLC-MS, and GC-MS. Despite being comprehensive in covering the determination of concurrent metabolites, these approaches have focused only on a representative metabolite or two for each of the BTEX com- Disclosed herein is a one-pot in situ derivatization kit or composition that can be directly integrated with LC-ESI-MS/MS for the simultaneous quantitation of 14 phenolic and carboxylic biomarkers of BTEX in human urine. Methods disclosed herein accommodates small volumes of urine samples, for example, 50 μL and can be fully automated and used as a single analytical platform to achieve short analysis time, high throughput, high sensitivity, and high specificity. Referring to FIG. 1, workflow sequence for a one-pot in situ derivatization kit according to one embodiment of the invention is shown. A mixture of 14 phenol and carboxylic acid biomarkers from BTEX metabolism is mixed with the chemicals of a reagent kit that comprises 2-FMP, 3-CMP, and TEA and keep at room temperature for 20 minutes to allow the 2-FMP, 3-CMP to derivatize the 14 biomarkers. 1% formic acid is then added to the reaction mixture to quench the reaction and 8 μL of the quenched mixture is injected through an auto sampler to a LC-MS for LC separation and (+) ESI-MS/MS analysis.

Figure 2A:
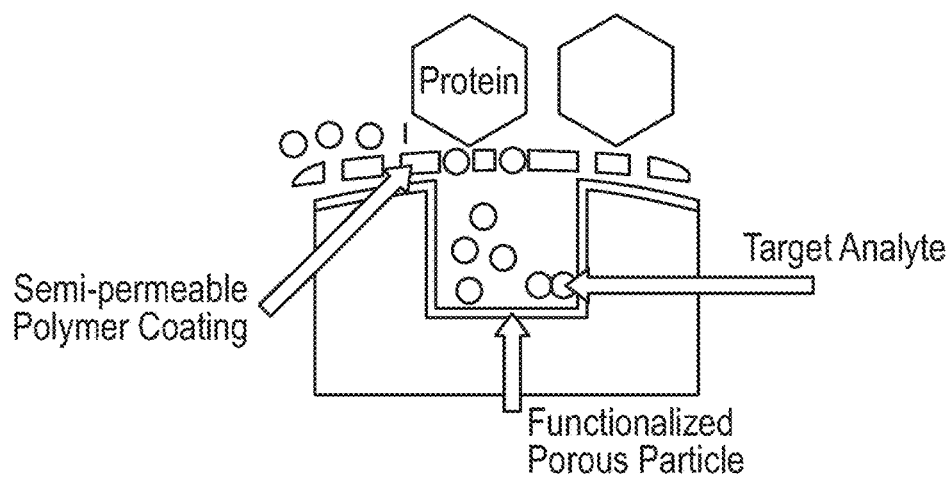
FIG. 2A illustrates the mechanism of a restricted access medium (RAM) trap column.
Figure 2B:
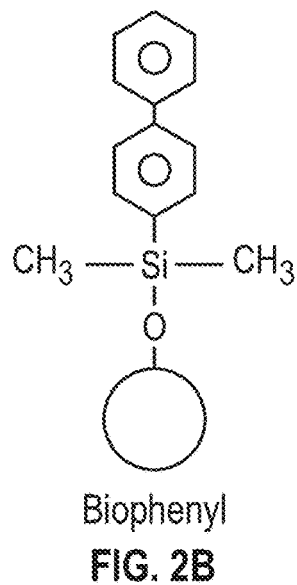
FIG. 2B illustrates surface chemistry of a biphenyl column.
Figure 2C:
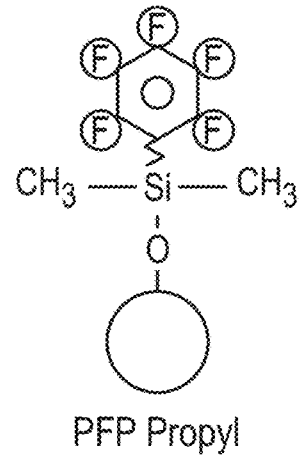
FIG. 2C illustrates surface chemistry of a pentafluorophenyl (PFP) propyl.

This derivatization reaction is a one-pot rapid reaction which occurs at room temperature and does not require any post-derivatization extraction or cleaning for high throughput analysis. However, depending on the purpose of study and complexity of sample matrix, the derivatization kit or composition can also employ traditional sample treatment methods such as liquid-liquid extraction and solid-phase extraction. Recent sample preparation methods, using restricted access media (RAM) or online SPE can also be used as a pretreatment. For example, online integration of weak cation exchange RAM for selective trapping and sample cleanup, using the method disclosed in Analytica chimica acta, 858 (2015) 74 to Beinhauer et al, incorporated herein by reference. FIG. 2A illustrates a RAM separation where protein is excluded by a semi-permeable polymer coating and target analytes enter the functionalized porous particle for separation. FIGS. 2B and 2C shows chromatography media functionalized by biphenyl and pentafluorophenyl propyl, respectively, that are effectively used for separation of the derivatized biomarkers for subsequent analysis.

Detection limits can additionally be improved simply by using a narrower I.D. column (e.g. 1 mm I.D.), multiple injection loading scheme &/or a more recent instrument (e.g. Shimadzu LC-MS 8050 or LC-MS 8060).

The compositions, kits, and methods disclosed herein can be used in many applications, for example, bio-monitoring in routine screening programs, large epidemiological, toxicological, and clinical studies. The methods disclosed herein can substitute a combination of analytical platforms for short and long-term effects of single and multiple BTEX exposures. Additionally, accurate detection of BTEX metabolite allows better understanding of the effects of exposure to BTEX compounds, which hopefully will enable preventive measures and evidence based practices by public health practitioners and health authorities to reduce or minimize BTEX exposure and related harmful health effects.

Low molecular weight polar metabolites usually suffer more background noise in the low mass spectral range. Hence, derivatization can result in an increase in their molecular weight to enable their detection in the high mass spectral range far from other matrix interferences. Moreover, phenols have very low ionization efficiencies when detected using the LC-ESI-MS, as they are neutral at the usual pH used for their LC-MS analysis. Carboxylic acids are usually detected in the negative ESI mode which is known to be less sensitive than positive ESI. Charge reversal derivatization of carboxylic acids to enable their detection using (+) ESI was reported to increase their sensitivity by 10- to 20-fold reported by Bollinger et al. in Analytical chemistry, 82 (2010) 6790 and by 2500-fold in another work conducted by Yang et al. in Analytical chemistry, 79 (2007) 5150, both of which are incorporated herein by reference. Other challenges for sensitive determination of carboxylic acids include their acidic character and high-water solubility which usually necessitates a compromise between increasing their chromatographic retention and resolution using acidic pH and increasing their ionization efficiencies using a basic pH for their LC-MS determination.

The fourteen targeted biomarkers of BTEX metabolism have various functionalities but all share either a carboxylic or phenolic functionality. Hence, to simultaneously increase their ionization efficiencies, we adopted the charge reversal derivatization kit or composition disclosed herein. In one embodiment, the kit or composition comprises 2-FMP, a charged alcohol 3-carbinol-1-methylpyridinium iodide (3-CMP), and a basic catalyst triethylamine. Phenol goes through a nucleophilic aromatic substitution to replace fluoride on the methylpyridium ring to form a positively charged pyridinium derivative of the phenol (PCP-P) as shown in FIG. 3A. Carboxylic acid goes through an in situ two step process to form a positively charged pyridinium derivative of the carboxylic acid (PCP-CA) as shown in FIG. 3B. In the first step, similar to phenol, the carboxylic acid goes through a nucleophilic aromatic substitution to replace fluoride on the methylpyridium ring of 2-FMP to form an intermediate pyridinium derivative of the carboxylic acid (IP-CA). The first step thus activates the carboxylic acid for subsequent charged esterification. In the second step, the charged alcohol 3-CMP replaces 2-FMP to form the positively charged pyridinium derivative of the carboxylic acid (PCP-CA). 2-FMP plays dual role by imparting a permanent positive charge that is unaffected by pH to phenols by forming charged ethers and at the same time activating the carboxylic acid functionalities for their charged ester formation with the charged alcohol 3-CMP.

The formed N-methylpyridyl ether ions $[M+92]^+$ for phenol and 3-carbinol-N-methyl pyridyl ester ions $[M+106]^+$ for all carboxylic acids except for muconic acid $[M+212]^{++}$, which has two derivatized carboxylic groups, are then amenable to sensitive detection by LC-(+)ESI-MS/MS. As shown in example 5, LOD can reach part-per-trillion levels for o-Cresols and part-per-billion levels for other biomarkers.

2-FMP used in the kit or composition is an example of a first pyridinium salt capable of forming a positively charged pyridinium derivative of the phenol (PCP-P) as well as an intermediate pyridinium derivative of the carboxylic acid (IP-CA). The first pyridinium salt has a structure of Formula I, where $Y=I^-$, $BF_4^-$

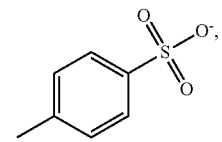

$R=$—$CH_3$ or —$C_2H_5$, and $X=F^-$, $Cl^-$ or $Br^-$

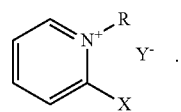

Formula I

3-CMP used in the kit or composition is an example of a second pyridinium salt capable of reacting with the IP-CA to form a positively charged pyridinium derivative of the carboxylic acid (PCP-CA). The second pyridinium salt has a structure of Formula II, where $R_1=$—$CH_3$ or —$C_2H_5$; $R_2=$—$CH_2$— or —$C_2H_4^-$; and $Y^-=I^-$ or $BF_4^-$.

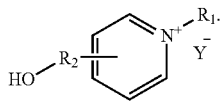

Formula II

Besides triethylamine, other amine based organic base can be used, including for example N,N-Diisopropylethylamine, tributylamine, trimethylamine.

To ensure all phenol and carboxylic acid in the sample is derivatized so that it can be detected, the amount of the first pyridinium salt in the kit or composition is at least 200 times the amount of the phenol in the sample, for example, 210, 220, 230, 240, 250, 260, 270, 280, 290, 300, 310, 320, 330, 340, 350, 360, 370, 380, 390, or 400 times. The amount of the second pyridinium salt in the kit or composition is at least 16 times the amount of the carboxylic acid in the sample, for example, 16, 17, 18, 19, 20, 21, 22, 23, 24, 25, 26, 27, 28, 29, 30, 31, 32 times. The amount of the organic base is at least about 0.01 times of the combined amount of the first and the second pyridinium salts, for example, 0.02, 0.03, 0.04, 0.0, 0.06, 0.07, 0.08, 0.09, 0.1, 0.11, 0.12, 0.13, 0.14, 0.15, 0.16, 0.17, 0.18, 0.19, 0.2 times.

In one embodiment, the kit or composition comprises about 21-35 mg/mL, for example, 22-34, 23-33, 24-32, 25-31, 26-30, 27-29 mg/mL of 2-Fluoro-1-methylpyridinium p-toluenesulfonate (2-FMP), about 24-40 mg/mL, for example, 25-39, 26-38, 27-37, 28-36, 29-35, 30-34, 31-33 mg/mL of 3-carbinol-1-methylpyridinium iodide (3-CMP), and about 4.5-7.5 µL, for example 5-7, 5.5-6.5 µL of triethyl amine. In this embodiment, the kit or composition is capable of derivatizing about 3.5 nanogram/mL to about 7.8 µg/mL of phenol and carboxylic acid.

Instead of in a kit format, a composition comprising the first pyridinium salt, the second pyridinium salt, and the organic base can be used to derivatize phenol and carboxylic acid in general. The derivatization can be carried out in a solution that contains significant amount of water, for example 50% of water.

EXAMPLES

Reagents and Chemicals

Triethylamine (TEA), phenol, 1,2-Dihydroxybenzene, o-cresol, p-cresol, trans, trans-muconic acid (MU), hippuric acid (HA), 2-methylhippuric (2MHA), 3-methylhippuric (3MHA), 4-methylhippuric acid (4MHA), phenylglyoxylic acid (PGA), DL-mandelic acid (MA), iodomethane, 3-pyridinemethanol and Surine™ negative urine control were purchased from Sigma-Aldrich (St. Louis, Mo.). DL-phenylmercaprturic acids (PMA), DL-benzylmercapturic acid (BMA), 2-Fluoro-1-methylpyridinium p-toluenesulfonate (2-FMP) and LC-MS grade formic acid were purchased from TCI America (Tokyo, Japan). Phenylglyoxylic Acid-d5 was purchased from Toronto research chemicals. N-Acetyl-S-benzyl-2,3,4,5,6-d5-DL-cysteine, trans, trans-Muconic-d4 Acid, 1,2-Dihydroxybenzene-d6, N-Benzoyl-d5-glycine, N-(2-Methyl-d3-benzoyl-d4)glycine, N-(3-Methyl-d3-benzoyl-d4)glycine, DL Mandelic-2,3,4,5,6-d5 Acid, N-Acetyl-S-phenyl-d5-DL-cysteine, o-Cresol-d7, p-Cresol-d7, Phenol-2,4,6-d3, Benzoic-d5 Acid were purchased from CDN Isotopes (Quebec, Canada). Pooled normal human urine was purchased from Innovative Research (Novi, Mich.). ClinChek® urine control was purchased from Recipe (Munich, Germany). LC-MS grade water, methanol and acetonitrile were purchased from Honeywell Burdick & Jackson International (Muskegon, Mich.).

Example 1 Synthesis of 3-carbinol-1-methylpyridinium iodide (3-CMP)

3-carbinol-1-methylpyridinium iodide (3-CMP) was synthesized in our lab adopting the scheme reported by Yang et al. in Analytical chemistry, 79 (2007) 5150. Briefly fivefold excess of methyl iodide (50 mmol) was mixed and shaken with 3-pyridine methanol (10 mmol) at room temperature for 1 h. The crystal formed were then washed with cold acetone and dried.

Example 2 Preparation of Stock Solutions and Other Validation Samples

Stock solutions of Phenol, MA, catechol, o-cresol, p-cresol were prepared in acetonitrile at a concentration of 2-3 mg·mL$^{-1}$. A standard mixture stock solution of HA (4 mg·mL$^{-1}$), 2MHA, 3MHA and 4MHA (each 2 mg·mL$^{-1}$), PGA (0.8 mg·mL$^{-1}$) and BA (0.1 mg·mL$^{-1}$) acids were prepared in acetonitrile:water mixture (8:2). Individual stocks of labeled and unlabeled PMA and BMA were prepared at 1 mg·mL$^{-1}$ in acetonitrile:water (9:1). MU labeled and unlabeled standards were prepared in acetonitrile:water (1:1) at 0.5 mg·mL$^{-1}$. The remaining deuterated analogs were prepared in acetonitrile at 1 mg·mL$^{-1}$. A working solution of deuterated internal standards (IS) was prepared from individual deuterated analog stocks. A series of working solutions of analytes were prepared from individual stocks by successive dilutions with acetonitrile and the calibration standards were then prepared by spiking 50 µL pooled human urine with 50 µL working solutions of the desired concentrations. Quality control (QC) samples were prepared in quintuplicate at low, medium and high concentration levels different from those concentrations used for the calibration points. Lab solutions software (version v.5.80, Shimadzu) was used for peak integration, calibration and quantification. Peak area ratios of analyte/IS were plotted versus the concentration ratios of analyte/IS and unknown concentrations were then calculated from the generated calibration curve equations.

Example 3 Preliminary Studies of In Situ Derivatization and Analysis

Figure 9:
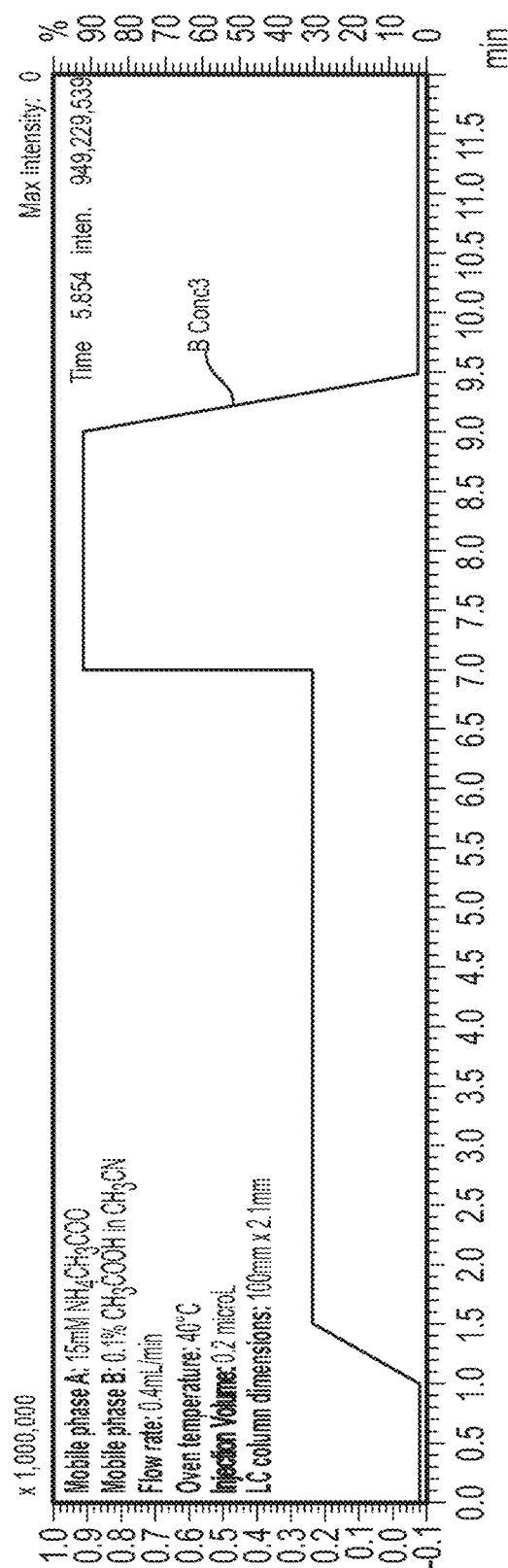
FIG. 9 shows mobile phase conditions and elution profile of derivatized BTEX metabolites according to Example 3.

A one-pot derivatization was adopted to directly derivatize target BTEX metabolites in their biological matrix. BTEX metabolites were successfully derivatized using a 2-fluoro-1-methyl pyridinium salt and 3-carbinol-1-methylpyridinium iodide. Derivatized metabolites were successfully separated and detected using LC-MS/MS. The details of the mobile phase conditions are listed in FIG. 9 and the optimized detection parameters for the derivatized analytes on the MS/MS system are shown in Table 2 below.

TABLE 2

Multiple Reaction Monitoring Settings for the Derivatized BTEX metabolites

| Peak ID | Derivatized Metabolite | MRM | Q1 Bias (V) | Collision Energy (V) | Q3 Bias (V) |
|---|---|---|---|---|---|
| 1 | Mandelic acid | 258.20 > 124.15, 258.20 > 107.00, 258.20 > 92.10 | −17 | −23 | −21 |
| 2 | Hippuric acid | 285.20 > 107.05, 285.20 > 124.10, 258.20 > 92.10 | −19 | −32 | −18 |
| 3 | 2-methylhippuric acid | 299.20 > 107.10, 299.20 > 124.10, 299.20 > 92.10 | −19 | −34 | −18 |
| 4, 5 | 3- & 4-methylhippuric acids | 299.20 > 107.10, 299.20 > 124.10, 299.20 > 92.10 | −20 | −33 | −18 |
| 6 | Phenol | 186.00 > 110.10, 186.00 > 177 10, 186.00 > 51.05 | −22 | −27 | −19 |
| 7 | t.t-Muconic acid | 177.20 > 107.10, 177.20 > 92.10, 177.20 > 65.10 | −12 | −21 | −18 |
| 8 | Catechol | 202.00 > 93.10, 202.00 > 186.05, 202.00 > 78.10 | −13 | −28 | −15 |
| 9 | Phenylmercapturic acid | 345.20 > 235.15, 345.20 > 107.10, 345.20 > 124.10 | −12 | −22 | −24 |
| 10 | Benzoic acid | 228.20 > 107.10, 228.20 > 105.05, 228.20 > 92.10 | −15 | −29 | −18 |
| 11 | Phenlglyxylic acid | 256.00 > 107.10, 256.00 > 92.10, 256.00 > 106.10 | −30 | −22 | −18 |
| 12 | O-Cresol | 200.10 > 91.10, 200.10 > 110.10, 200.10 > 65.10 | −13 | −27 | −15 |
| 13 | P-Cresol | 200.00 > 110.10, 200.00 > 91.10, 200.00 > 65.10 | −23 | −26 | −19 |
| 14 | Benzylmercapturic acid | 359.20 > 235.15, 359.20 > 107.10, 359.20 > 124.15 | −24 | −24 | −24 |

Example 4 In Situ Derivatization and Direct Analysis

A 50 µL of centrifuged urine was mixed with an equal volume of standards (STDs) in auto sampler glass vials followed by the addition of 25 µL of internal standard solution. 200 µL, of 2-FMP (28 mg/mL), 200 µL of CMP (32 mg/mL) and 6 µL of TEA were then successively added to the reaction vial. The derivatization reaction was briefly vortexed and then allowed to proceed for 20 min at room temperature. After 20 min, 469 µL of 1% formic acid in water was added to the reaction mixture to quench the derivatization reaction. The auto sampler vial was then transferred to the auto sampler for LC-MS/MS analysis. For unknown urine samples, the same procedure was adopted except no standards were spiked and instead a 50 µL of acetonitrile:water (95:5) was added.

An upgraded Shimadzu LCMS-8030 (Shimadzu Scientific Instruments, Inc., Columbia, Md.) was employed for the LC-MS/MS analysis. The triple quadrupole was operated using positive ionization ESI and scheduled multiple reaction monitoring (SMRM) modes. The mass spectrometer conditions were as follows: Interface voltage, 4.5 kV; nebulizer gas, nitrogen at 3 L/min; heat block temperature, 300° C.; desolvation line (DL) temperature, drying gas, nitrogen at 13 L/min; and collision gas, argon at 230 kPa. The MRM events used for quantitation, confirmation and internal standards are summarized in the table of FIG. 4.

LC was performed using a binary solvent delivery system (LC-20AD XR, Shimadzu) and auto sampler (SIL-20ACXR, Shimadzu). The mobile phase consisted of 0.1% formic acid in water as solvent A and 0.1% formic acid in methanol as solvent B. Gradient elution started initially with 0% B for 1.5 min, then increasing linearly from 50% B to 54% B over 5.5 min, followed by a 0.5 min hold at 100% B and finally equilibrating at 0% B for 5 min. A flow rate of 0.3 mL min$^{-1}$ was used and increased to 0.4 mL min$^{-1}$ during the time interval from 7 to 10 min. The column oven temperature was set to 9° C. Chromatographic separations were performed using a Force™ Biphenyl (Restek Corporation, Bellefonte, Pa.) (2.7 µm dp; 100×2.1 mm) column (biphenyl bonded phase on a fully porous silica particle). Sample injection volume was 8 µL. Total LC run time was 12.5 min including the washing and equilibration steps.

Figure 5:
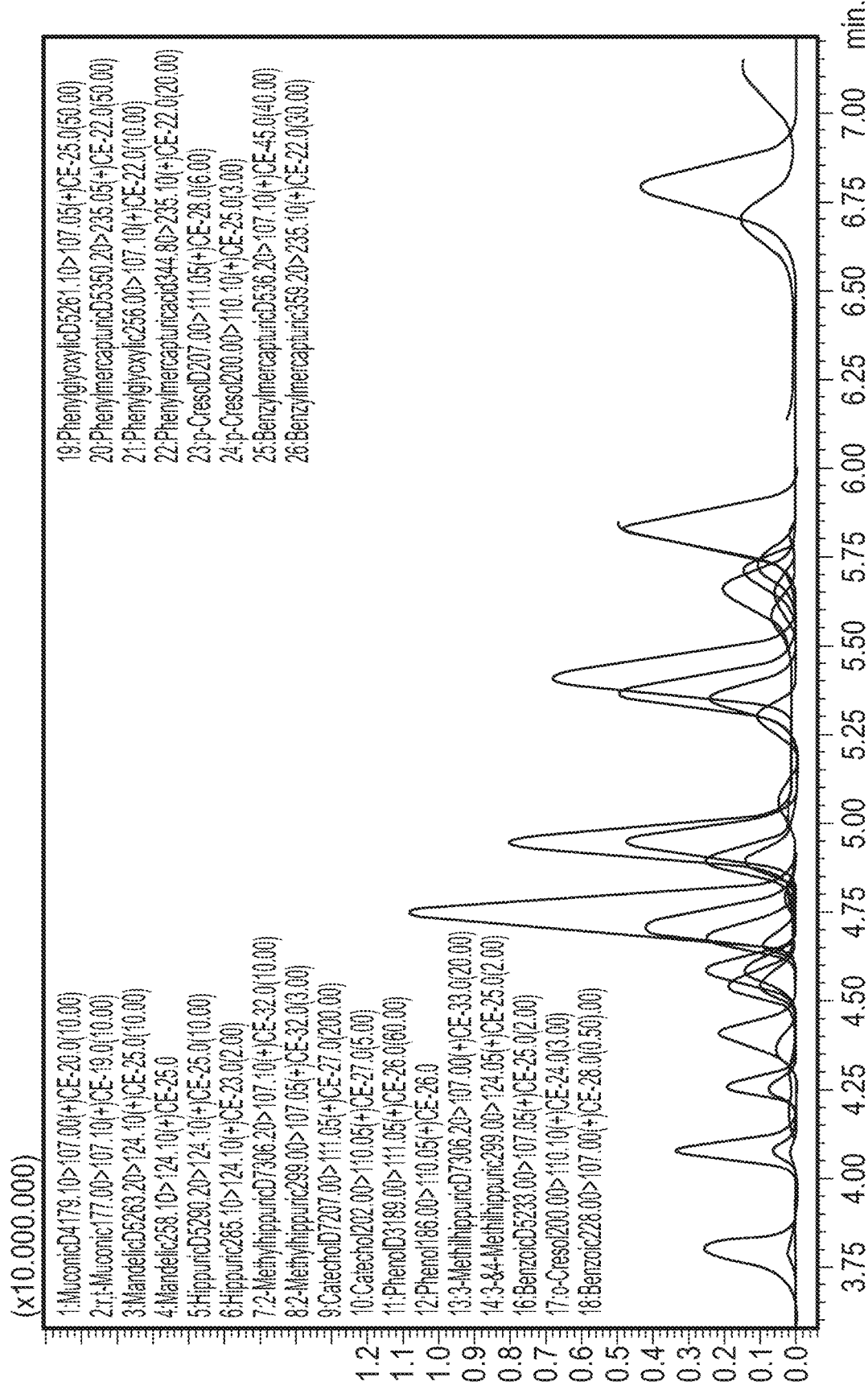
FIG. 5 shows the chromatogram of BTEX metabolite separation according to one embodiment of the invention.

Although all derivatized biomarkers are polar and cationic, adopting the hydrophilic interaction liquid chromatography (HILIC) mode using either silica or pentafluorophenyl chemistry (data not shown) was proven to be inefficient of achieve baseline resolution of important isomers under study (o- & p-cresols and 2-, 3- and 4-MHA). Moreover, the elution occurred at relatively high aqueous conditions to decrease the LC run time which cancelled the usual gained advantage of high sensitivity by using HILIC mode. LC method using biphenyl chemistry is adopted to take advantage of the cation-π interaction, and a low oven temperature of 9° C. to add additional shape selectivity which led to baseline resolving positional isomers (except 3- & 4-MHA) under study and other matrix interferences. These conditions also achieved a high sensitivity by eluting all biomarker in high organic % window of 50%-54% methanol as shown in FIG. 5.

Example 5 Optimization of Derivatization Kit or Composition Variables

Parameters affecting the performance of the kit or composition disclosed herein include concentration of FMP, concentration of CMP and volume of TEA. Central composite design (CCD) was used to optimize the values of these three factors and to achieve the best response using Surine™ samples spiked with standard mixture. The CCD is divided into three groups of design points: a two-level factorial design points for estimating first order and two-factor interactions, star points for estimating quadratic effects and replicates of center points estimating pure error and to tie blocks as disclosed in "RSM simplified: optimizing processes using response surface methods for design of experiments, CRC press, 2004" by Whitcomb & Anderson as well as in "DOE simplified: practical tools for effective experimentation, CRC Press, 2015" by Anderson & Whitcomb. The other variables such as reaction temperature and time were also evaluated. In one embodiment, the reaction was carried out for 20 minutes at room temperature. The employed CCD included 20 experiments in five levels for three factors and consisted of six replicates of center points.

All injections were made in triplicate (n=3) and in random order to provide protection against bias from variables which change over time. The experimental design was further divided into two blocks to remove effects of unknown or uninterested variables on response which can vary from day to day. Four individual responses, representative of the fourteen biomarkers, were chosen to evaluate the derivatization yield efficiency. These responses were the peak areas of muconic acid, 3MHA+4MHA, PMA and catechol. Design-Expert® software version 10 (Stat-Ease, Minneapolis, USA) was employed to perform experimental design and the statistical analysis.

The significance of the regression models was evaluated by applying the analysis of variance (ANOVA) and eliminating the statistically insignificant parameters (p-value larger than 0.05). The lack-of-fit (LOF) values for all models were not significant relative to the pure error as indicated by their p-values. Final predictive polynomial equations for the chosen models were calculated and listed in the table of FIG. 6 in terms of coded values. The coefficients for the significant factors selected in each polynomial model are shown based on coded factors (−1 to +1 for the low versus high levels) to show a direct comparison of the relative impact of different factors on the predicted response by each model for each response. Response transformations were applied for the responses of catechol and muconic acid to improve their predictive models and to stabilize variance across the whole range of responses.

Figure 7:
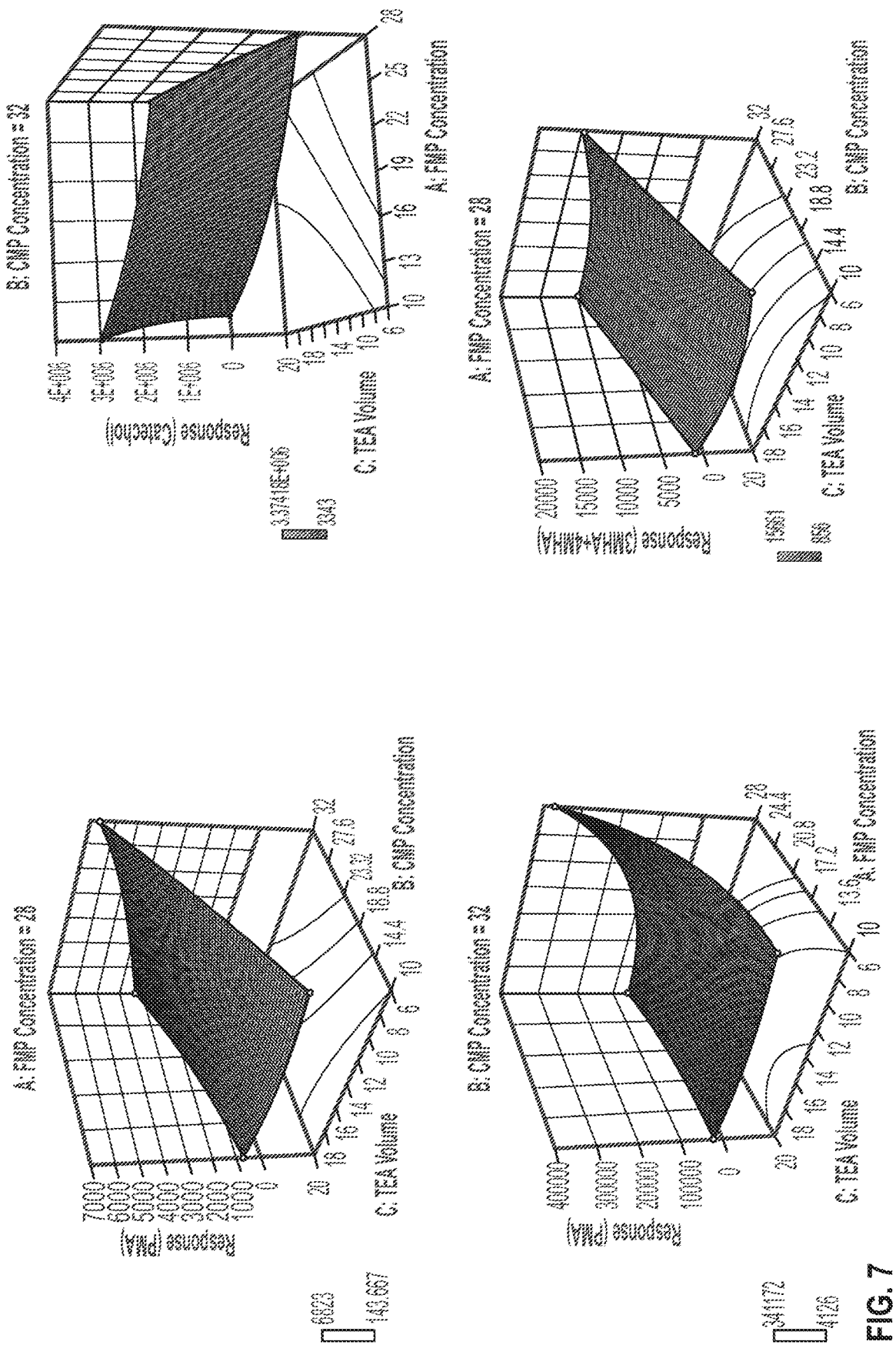
FIG. 7 shows 3D response surface plots of a factorial design to determine the kit parameters according to one embodiment of the invention.
Figure 8A:
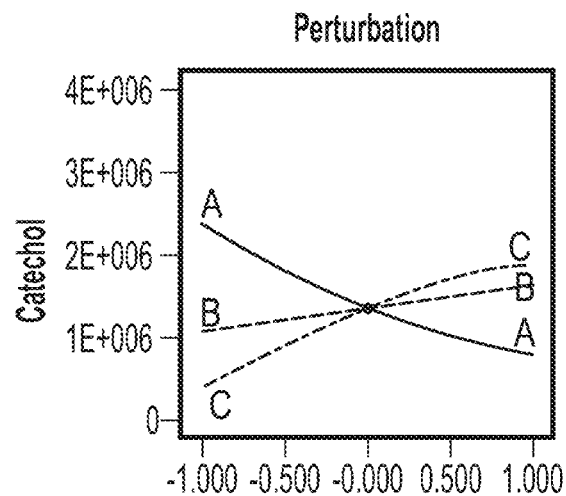
FIG. 8 shows perturbation plots illustrating the relative significance of individual derivatization kit or composition parameters on the responses of (a) catechol, (b) methylhippuric acids, (c) phenylmercapturic acid and (d) muconic acid.
Figure 8C:
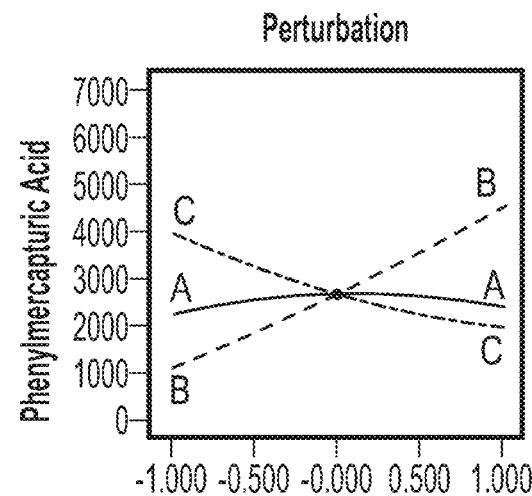
Figure 8B:
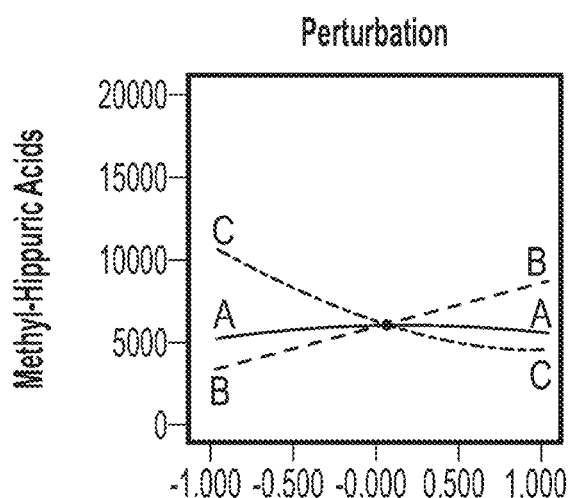
Figure 8D:
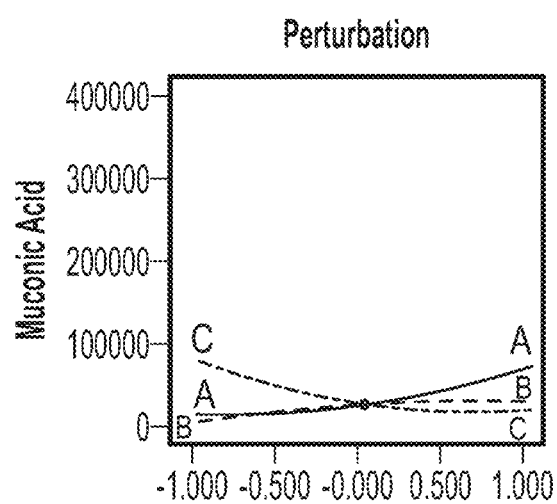

3D Response surface plots for each one of the four target responses were generated in FIG. 7 to find regions of maximum yields. Perturbation plots illustrating the relative significance of individual derivatization kit or composition parameters on the responses of (a) catechol, (b) methylhippuric acids, (c) phenylmercapturic acid, and (d) muconic acid are shown in FIG. 8.

As can be easily noted, since the factor levels required to achieve optimum response values for carboxylic metabolites do not correspond with those required for catechol as a representative of phenolic metabolites, then a compromise among the responses should be achieved. The desirability function can be used to achieve the compromise when dealing with multiple responses as discussed in "DOE simplified: practical tools for effective experimentation, CRC Press, 2015" by Anderson & Whitcomb, incorporated herein by reference. In one embodiment, the derivatization conditions in terms of desirability score were achieved at the following values: 28 mg mL$^{-1}$ FMP, 32 mg mL$^{-1}$ CMP and 6 μL TEA, which were adopted to carry out model confirmation for each metabolite as demonstrated in Table 3.

TABLE 3

| | Confirmation results for predictive models | | | | |
|---|---|---|---|---|---|
| Response | Predicted Mean | N[a] | 95% PI[b] low | Data Mean | 95% PI[b] high |
| Catechol | 209714.0 | 3 | 94627.5 | 208532.0 | 359043.0 |
| PhenylMercapturic acid | 6599.3 | 3 | 5471.5 | 7627.1 | 7727.1 |
| Muconic acid | 374833.0 | 3 | 173637.0 | 309420.0 | 722600.0 |
| MethylHippuric acids | 15350.1 | 3 | 12882.5 | 17295.1 | 17817.7 |

[a]N: Number of replicates, each injected three times.
[b]PI: prediction interval.

To ensure that the method was suitable for application in routine urine analysis, the basic analytical performance parameters such as calibration curves, linearity, limits of detection (LODs), precision, accuracy and stability of derivatized urine samples were evaluated and determined. Isotope dilution mass spectrometry calibration was chosen for quantitation, and the validity of the novel method was demonstrated by analysis of ClinChek® Urine controls (available as two different spiked levels for each analyte) for seven of the biomarkers under study.

At least six non-zero standard solutions were analyzed to obtain calibration curves with linear regression. A characteristic quantifier ion of each analyte was chosen, and its authenticity was verified with two qualifier ions. The response of the quantifier ion was normalized to the response of the corresponding deuterated analogs. The limits of detection (LOD) were calculated experimentally as the smallest concentration of each analyte which gave signal to noise ratio of 3 and then by dilution 2-3 fold the signal disappears. We did not calculate LOD for analytes which have minimum background levels since these will not indicate the actual LOD and their zero concentration responses were included for plotting their calibration curves. Excellent linear responses were achieved for all analytes ($R^2 \geq 0.990$) where either a quadratic fit or a linear fit was employed with or without weighting of 1/c. LOD were calculated both as native concentration of biomarkers in urine and as the mass loaded on column (after applying a dilution factor of 20) to show the actual performance concerning the sensitivity of the method. Recoveries at the three QC concentration levels ranged from 85 to 114% and RSD % were within 14% for all biomarkers. The proposed method was successfully applied to the analysis of the ClinChek® urine control samples as shown in Table 4. The stability of the derivatized urine samples was studied over a period of 24 hours at room temperature and in the auto sampler at 4° C. by injecting high QC samples in triplicate. The LC-MS/MS results showed that the derivatized urine samples were stable with <5% change in their concentration.

TABLE 4

Method validation and Application to ClinChek Urine Controls

| Analyte | Calibration range μg mL$^{-1}$ ($R^{2*}$) | LOD in sample (μg mL$^{-1}$) | LOD on column (pg) | Spiked Concentration (μg mL$^{-1}$) | Measured Concentration (μg mL$^{-1}$) (Accuracy % ± RSD) | ClinChek® Level I Reference concentration range (μg mL$^{-1}$) | ClinChek® Level I Measured values (Mean concentration ± RSD) | ClinChek® Level II Reference concentration range (μg mL$^{-1}$) | ClinChek® Level II Measured values (Mean concentration ± RSD) |
|---|---|---|---|---|---|---|---|---|---|
| MU | 0-25 (0.997) | | | 20.0 | 106 ± 7 | 0.7-1.2 | 1 ± 14 | 2.4-3.6 | 2.8 ± 5 |
| | | | | 3.6 | 97 ± 10 | | | | |
| | | | | 1.3 | 98 ± 11 | | | | |
| MA | 9.4-500 (0.990) | 1.6 | 640 | 480.0 | 91 ± 4 | 123-185 | 159 ± 10 | 430-645 | 458 ± 2 |
| | | | | 85.7 | 105 ± 10 | | | | |
| | | | | 30.0 | 113 ± 10 | | | | |
| HA | 0-1996 (0.999) | | | 1596.8 | 112 ± 5 | 345-467 | 351 ± 6 | 1470-1990 | 1796 ± 4 |
| | | | | 285.1 | 110 ± 6 | | | | |
| | | | | 99.8 | 105 ± 9 | | | | |
| 2MHA | 15.6-1000 (1.000) | 7.8 | 3120 | 800.0 | 114 ± 4 | 138-207 | 167 ± 4 | 246-332 | 301 ± 6 |
| | | | | 142.9 | 91 ± 14 | | | | |
| | | | | 50.0 | 106 ± 11 | | | | |
| 3MHA + 4MHA | 5.3-2032 (0.998) | 5.3 | 2120 | 1625.6 | 109 ± 2 | 456-683 | 508 ± 4 | 814-1101 | 907 ± 8 |
| | | | | 101.6 | 113 ± 6 | | | | |
| | | | | 33.9 | 85 ± 12 | | | | |
| BA | 0-50 (0.998) | | | 40.0 | 103 ± 2 | | | | |
| | | | | 7.1 | 106 ± 1 | | | | |
| | | | | 0.8 | 100 ± 1 | | | | |
| PGA | 12.5-400 (0.994) | 3.1 | 1240 | 320.0 | 111 ± 6 | 47.8-71.7 | 52 ± 10 | 144-215 | 147 ± 27 |
| | | | | 57.1 | 101 ± 11 | | | | |
| | | | | 20.0 | 100 ± 10 | | | | |
| PMA | 1.6-100 (0.995) | 0.8 | 320 | 80.0 | 107 ± 7 | | | | |
| | | | | 14.3 | 103 ± 3 | | | | |
| | | | | 5.0 | 99 ± 11 | | | | |
| BMA | 0.5-60 (1.000) | 0.2 | 80 | 48.0 | 102 ± 7 | | | | |
| | | | | 8.6 | 98 ± 6 | | | | |
| | | | | 1.0 | 97 ± 4 | | | | |
| Phenol | 0-60 | | | 48.0 | 97 ± 3 | | | | |
| | | | | 3.0 | 93 ± 4 | | | | |
| | | | | 1.0 | 97 ± 5 | | | | |
| Catechol | 0.3-134 (0.999) | 0.1 | 40 | 107.2 | 95 ± 8 | | | | |
| | | | | 19.1 | 103 ± 5 | | | | |
| | | | | 2.2 | 90 ± 12 | | | | |
| o-cresol | 0.01-4 (0.991) | 0.0035 | 1.4 | 3.2 | 97 ± 3 | | | | |
| | | | | 0.6 | 99 ± 3 | | | | |
| | | | | 0.1 | 103 ± 10 | | | | |
| p-cresol | 0-4 (0.996) | | | 3.2 | 97 ± 3 | | | | |
| | | | | 0.2 | 109 ± 6 | | | | |
| | | | | 0.1 | 101 ± 6 | | | | |

Example 6 RAM Efficiency

Figure 10:
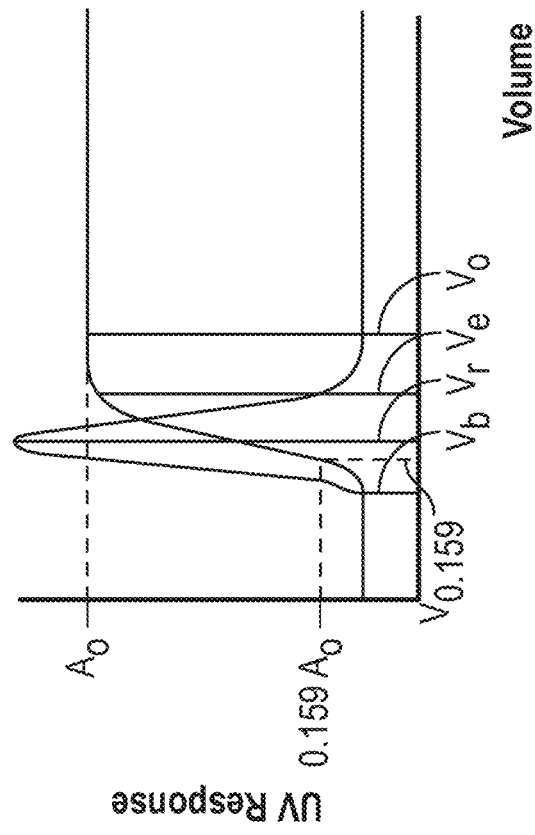
FIG. 10 shows a typical breakthrough curve and its first derivative showing the characteristic chromatographic parameters that characterize RAM trapping.

A RAM trap column was used for the online isolation and pre-concentration of four model compounds with different physicochemical properties. Different flow rates of 0.25, 0.5, 1 and 2 mL/min using 98:2 0.5% acetic acid in water:methanol or 5 mM ammonium acetate in water:methanol as mobile phases were used for evaluation of small molecule trapping efficiency. Breakthrough curves acquisition through frontal analysis was analyzed to determine frontal chromatographic parameters specific for each of the studied compounds. FIG. 10 shows a typical breakthrough curve and its first derivative showing the characteristic chromatographic parameters that characterize RAM trapping. Evaluation of RAM trapping by frontal analysis shows that different compounds with different physicochemical characteristics have different trapping efficiencies as shown in Table 5 below. Using various flow rates of 0.25, 0.5, 1 and 2 mL/min did not have any significant effect on changing the experimental values of $V_b$ of studied compounds on different studied trap columns. Using the low flow rate of 0.25 mL/min achieved the best trapping efficiency. MAYI trap C4 and C8 columns gave the highest values of efficiency and in most cases had very close values of efficiency. MAYI trap C18 had the lowest efficiency except for Dopamine HCl (highest hydrophilic) where it gave values close to that of C4 and C8 trap columns.

TABLE 5

Evaluations of RAM trapping by Frontal Analysis

| Analyte | RAM | $N_{Gaussian}{}^a$ | $N_{Frontal}{}^b$ | Trapping Capacity ($V_{b1}$ mL) | Saturation Capacity ($V_{e1}$ mL) |
|---|---|---|---|---|---|
| Dopamine | C4 | 48.56 | 50 | 0.42 | 0.73 |
| | C8 | 49.43 | 53.21 | 0.42 | 0.73 |
| | C18 | 52.51 | 50.5 | 0.45 | 0.78 |
| Acetaminophen | C4 | 80 | 69.5 | 1.39 | 2.14 |
| | C8 | 82.25 | 67.63 | 1.26 | 1.98 |
| | C18 | 56.42 | 34.65 | 1.19 | 2.23 |
| 4-Hydroxy benzoic acid | C4 | 152.44 | 81.49 | 1.94 | 2.93 |
| | C8 | 148.85 | 107.83 | 2.14 | 3.11 |
| | C18 | 44.68 | 19.21 | 1.87 | 4.03 |
| Diethyl Phthalate | C4 | 1062.8 | 493.16 | 50.88 | 59.54 |
| | C8 | 723.59 | 444.95 | 52.08 | 61.58 |
| | C18 | NA | 53.71 | 45.25 | 68.42 |

The embodiments above are intended to be illustrative and not limiting. Additional embodiments are within the claims. In addition, although the present disclosure has been described with reference to particular embodiments, those skilled in the art will recognize that changes can be made in form and detail without departing from the spirit and scope of the disclosure. Any incorporation by reference of documents above is limited such that no subject matter is incorporated that is contrary to the explicit disclosure herein.

The invention claimed is:

1. A composition for derivatizing phenol and carboxylic acid simultaneously in an aqueous sample, the composition comprising:
a first pyridinium salt that forms a positively charged pyridinium derivative of the phenol (PCP-P) and an intermediate pyridinium derivative of the carboxylic acid (IP-CA);
a second pyridinium salt that reacts with the IP-CA to form a positively charged pyridinium derivative of the carboxylic acid (PCP-CA);
an organic base; and
a quencher;
wherein the first pyridinium salt has a structure of Formula I, wherein $Y=BF_4^-$ or

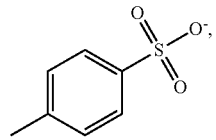

$R=-CH_3$ or $-C_2H_5$, and $X=F^-$ or $Cl^-$,

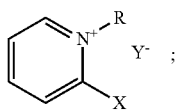

Formula I wherein the second pyridinium salt has a structure of Formula II, wherein $R_1=-CH_3$ or $-C_2H_5$; $R_2=-CH_2-$ or $-C_2H_4-$; and $Y^-=I^-$ or $BF_4^-$,

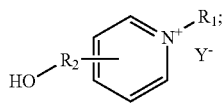

Formula II and
wherein the amount of the first pyridinium salt is at least 200 times higher than the phenol amount in the sample, the amount of the second pyridinium salt is at least 16 times higher than the carboxylic acid amount, and the amount of the organic base is at least about 0.01 times of the combined amount of the first and the second pyridinium salt.

2. The composition of claim 1, wherein the organic base is selected from a group consisting of triethyl amine, N,N-Diisopropylethylamine, tributylamine, trimethylamine.

3. The composition of claim 1, wherein the first pyridinium salt is 2-Fluoro-1-methylpyridinium p-toluenesulfonate (2-FMP), the second pyridinium salt is 3-carbinol-1-methylpyridinium iodide (3-CMP), and the organic base is triethyl amine (TEA).

4. The composition of claim 1, wherein the composition is capable of derivatizing about 3.5 nanogram/mL to about 7.8 µg/mL of phenol and carboxylic acid and the first pyridinium salt is 21-35 mg/mL of 2-fluoro-1-methylpyridinium ptoluenesulfonate (2-FMP), the second pyridinium salt is 24-40 mg/mL of 3-carbinol-1-methylpyridinium iodide (3-CMP), and the organic base is 4.5-7.5 µL of triethyl amine.

5. The composition of claim 1, wherein the composition comprises about 28 mg/mL of 2-fluoro-1-methylpyridinium p-toluenesulfonate (2-FMP) in acetonitrile, about 32 mg/mL of 3-carbinol-1-methylpyridinium iodide (3-CMP) in acetonitrile, and about 6 µL of triethyl amine (TEA).

6. The composition of claim 1, wherein the quencher is formic acid.

* * * * *